United States Patent
Inoue et al.

(10) Patent No.: US 9,772,286 B2
(45) Date of Patent: Sep. 26, 2017

(54) METHOD FOR DETECTION OF UROTHELIAL CANCER

(75) Inventors: Keiji Inoue, Kochi (JP); Taro Shuin, Kochi (JP); Mutsuo Furihata, Kochi (JP); Yoshihiko Hirao, Osaka (JP); Tohru Tanaka, Tokyo (JP)

(73) Assignees: SBI Pharmaceuticals Co., Ltd., Tokyo (JP); National University Corporation Kochi University, Kochi (JP)

( * ) Notice: Subject to any disclaimer, the term of this patent is extended or adjusted under 35 U.S.C. 154(b) by 321 days.

(21) Appl. No.: 13/703,829

(22) PCT Filed: Jun. 20, 2011

(86) PCT No.: PCT/JP2011/003509
§ 371 (c)(1),
(2), (4) Date: Dec. 12, 2012

(87) PCT Pub. No.: WO2011/161933
PCT Pub. Date: Dec. 29, 2011

(65) Prior Publication Data
US 2013/0095520 A1  Apr. 18, 2013

(30) Foreign Application Priority Data

Jun. 21, 2010  (JP) .................................. 2010-140348

(51) Int. Cl.
| | |
|---|---|
| *G01N 21/64* | (2006.01) |
| *G01N 33/574* | (2006.01) |
| *G01N 33/58* | (2006.01) |
| *A61K 49/00* | (2006.01) |
| *A61K 41/00* | (2006.01) |

(52) U.S. Cl.
CPC ... *G01N 21/6486* (2013.01); *G01N 33/57407* (2013.01); *G01N 33/57434* (2013.01); *G01N 33/57438* (2013.01); *G01N 33/582* (2013.01); *A61K 41/0061* (2013.01); *A61K 49/0021* (2013.01); *A61K 49/0036* (2013.01); *G01N 21/6428* (2013.01); *G01N 21/6458* (2013.01)

(58) Field of Classification Search
None
See application file for complete search history.

(56) References Cited

U.S. PATENT DOCUMENTS

2005/0031541 A1* 2/2005 Gierskcky et al. ............ 424/9.6
2008/0108701 A1* 5/2008 Okura et al. .................. 514/561

FOREIGN PATENT DOCUMENTS

| JP | 2006-124372 A | 5/2006 |
| WO | WO 91/01727 | 2/1991 |
| WO | WO 2009/130893 A1 | 10/2009 |
| WO | WO 2009130893 | * 10/2009 |
| WO | WO 2011/161933 A1 | 12/2011 |

OTHER PUBLICATIONS

Hurwitz et al., downloaded on Dec. 23, 2016 from http://www.cancernetwork.com/cancer-management/urothelial-and-kidney-cancers.*
Fujimoto et al., "Fluorescence Cystoscopy-Assisted Transurethral Resection of Bladder Tumor and Photodynamic Diagnosis of Exfoliated Cells in the Urine using 5-Aminolevulinic Acid in Bladder Cancer", The Journal of Japan Society for Laser Surgery and Medicine, Jan. 30, 2010, vol. 30, No. 4, 7 pages.
Inoue et al., "Clinical Experience with Intravesical Instillations of 5-Aminolevulinic Acid (5-ALA) for the Photodynamic Diagnosis Using Fluorescence Cystoscopy for Bladder Cancer," The Japanese Journal of Urology, 2006, vol. 97, No. 5, 11 pages.
Fujimoto et al., "Photodynamic Diagnosis of Bladder Cancer," The Japanese Journal of Urgology, vol. 101, No. 2, Annual Meeting Special Issue, Feb. 2010, 4 pages.
European Search Report from corresponding EP Application No. 11797822.1 dated Oct. 29, 2013, 5 pages.
Tauber et al., "Fluoreszenzzytologie der Harnblase [Fluorescencezytology of the Urinary Bladder]", Urologe Ausgabe A, Springer, Berlin, DE, vol. 40, No. 3, Jan. 1, 2001, pp. 217-221.
Pytel et al., "New Aspect of Photodynamic Diagnosis of Bladder Tumor: Fluorescence Cytology", Urology, Belle Mead, NJ, US, vol. 59, No. 2, Feb. 1, 2002, pp. 216-219.
Hattori et al., "Cytological Analysis of Catheterized Urine By Using an Image Analysis Device-Differential Diagnosis Between G1 Transitional Cell Carcinoma and Benign Disease," The Journal of the Japanese Society of Clinical Cytology, vol. 36 (1997) No. 3, 8 pages.

* cited by examiner

*Primary Examiner* — Jennifer Pitrak McDonald
*Assistant Examiner* — Qing Xu
(74) *Attorney, Agent, or Firm* — Cadawalder, Wickersham & Taft LLP

(57) ABSTRACT

It is to provide a method for detecting urothelial cancer simply and with high accuracy. It is a method for detecting urothelial cancer comprising administering 5-aminolevulinic acid (ALA), a derivative thereof, or a salt of these to a test subject, collecting urine from the test subject, and detecting the presence of fluorescence or amount of fluorescence in the collected urine.

9 Claims, 2 Drawing Sheets

[Fig. 1]
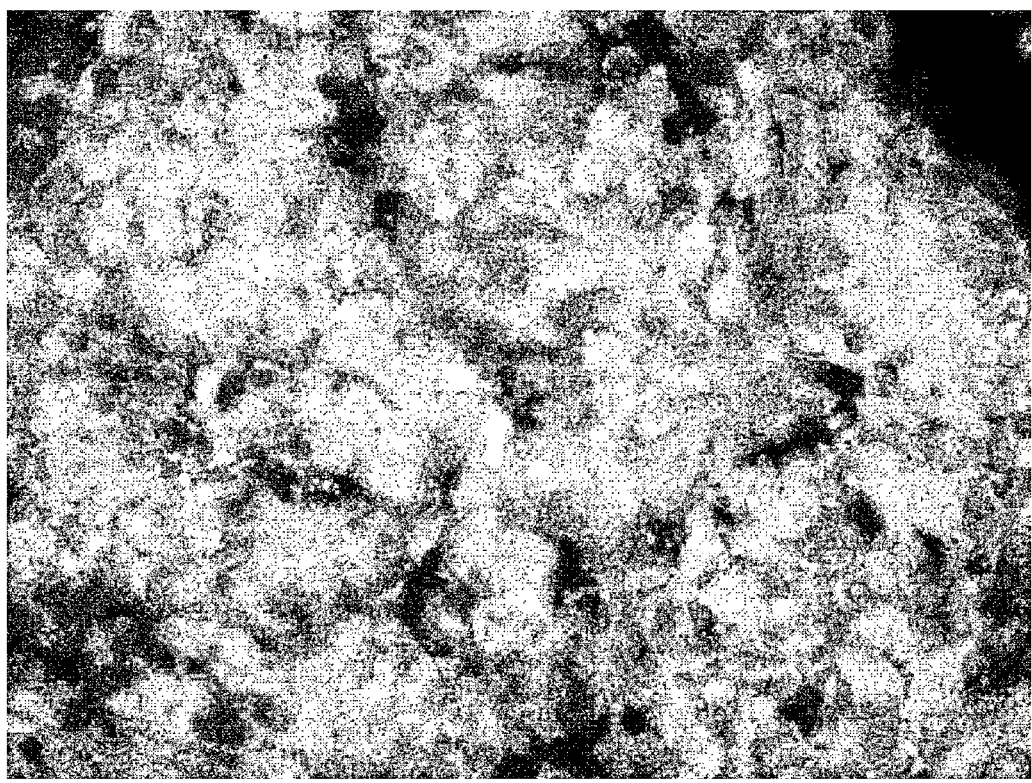

[Fig. 2]
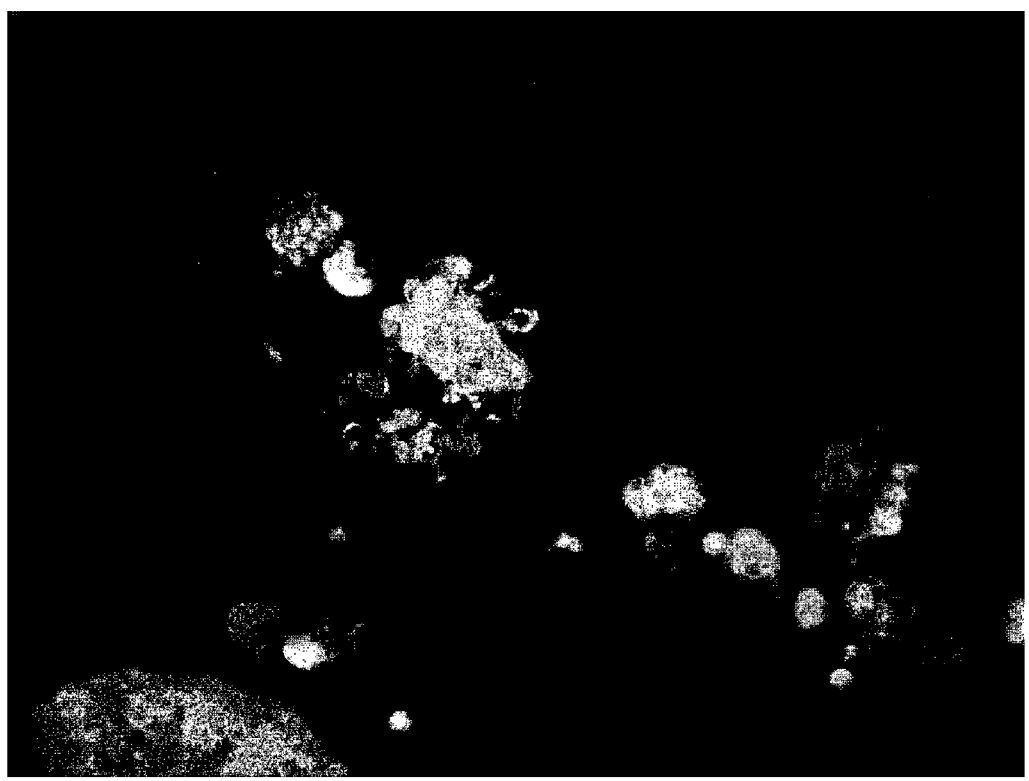

METHOD FOR DETECTION OF UROTHELIAL CANCER

TECHNICAL FIELD

The present invention relates to a method for detecting urothelial cancer, specifically to a method for detecting urothelial cancer using 5-aminolevulinic acid (ALA), a derivative thereof, or a salt of these (hereinafter may be referred to as "ALAs").

BACKGROUND ART

Examination of urothelial cancer is usually performed by staining cells dropped out in the urine by Papanicolaou stain and observing them with a microscope. However, proficiency is required to diagnosis, and there are often oversights, which is a problem. The difficulty of detection leads to the delay in cancer detection, and thus to miss relapse.

On the other hand, in the endoscopic operation for a bladder cancer patient, it is known to inject ALAs into bladder, observe the fluorescence derived from cancer cells in the bladder to determine the excision site (see for example, Nonpatent Document 1). It is also known that the observation of fluorescence in the bladder is possible by administering orally or injecting intravenously ALAs (see Patent Document 1).

Further, a diagnostic agent for tumor comprising ALAs is proposed, which agent is intended to determine the presence or absence of tumor in tissues of brain, nasal tract, nasal cavity, trachea, bronchi, buccal cavity, pharynx, esophagus, stomach, breast, colorectum, lung, ovary, central nervous system, liver, bladder, urethra, urinary duct, pancreas, cervical duct, abdominal cavity, anal duct, or cervix uteri, by administering the diagnostic agent for tumor in an amount of 0.001 mg to 10 g per kg of body weight at a time, measuring protoporphyrin IX, uroporphyrin I, coproporphyrin I, etc. in a sample collected in vivo or in vitro such as blood, body fluid, tissue, urine, feces, saliva, sweat, spinal fluid, seminal fluid, or tears to diagnose tumor (see for example Patent Document 2).

Further a PDD cytology method targeting fluorescence exfoliated cells in the urine, comprising performing fluorescence cytology and flow cytometry for detecting ALA-induced fluorescence positive cells is reported, which method comprises in vitro incubation method comprising dissolving urinary sediment collected from a bladder cancer patient into a serum free culture solution with an ALA concentration adjusted to 200 μg/mL, and keeping the heat at 37° C. for 2 hours in a dark room before subjecting the resultant to the test; and in vivo incubation method subjecting the urinary sediment collected from ALA solution (1.5 g ALA/50 mL buffer) kept in the bladder of a bladder cancer patient for 2 hours to the test (see for example Nonpatent Document 2).

PRIOR ART DOCUMENTS

Patent Documents

Patent Document 1: WO2009/130893
Patent Document 2: Japanese unexamined Patent Application Publication No. 2006-124372

Nonpatent Documents

Nonpatent Document 1: "Photodynamic diagnosis of bladder cancer using fluorescent cystoscope by bladder instillation of 5-aminolevulinic acid (5-ALA)"; Hirofumi Inoue, Hisashi Karashima, Masayuki Kamata, Taro Shuin, Mutsumi Kurabayashi, Yuji Otsuki; Journal of the Japanese Urological Association, Vol. 97, pp. 719-729

Nonpatent Document 2: "Photodynamic diagnosis of bladder cancer—usefulness of fluorescence cytology—"; Kiyohide Fujimoto, Makito Miyake, Kiyoshi Nakai, Yoshiaki Matsumura, Satoshi Anai, Yoshihiko Hirao; The Japanese Urological Association, Vol. 101, No. 2, General Assembly Special Edition, February 2010

SUMMARY OF THE INVENTION

Object to be Solved by the Invention

As it is stated in the above, conventional examination of urothelial cancer required proficiency, having problems to often overlook the disease, a novel and simple technique with high accuracy was awaited. For example, in the in vitro incubation, a culture apparatus to culture under dark was necessary, and the patient had to wait many hours to obtain the results after urine collection. In the in vivo incubation, there was a problem to cause burden to the patient when injecting ALA solution in the bladder, and that the detection was limited to bladder cancer.

The object of the present invention is to provide a method for detecting urothelial cancer that can detect urothelial cancer simply and with high accuracy, without need of a particular culture apparatus, and allowing determination just after urine collection.

Means to Solve the Object

The present inventors made a keen study with an idea that a technique using ALAs such as described in the above can be applied to cytology of urothelial cancer, and found out that by detecting fluorescence in free cancer cells in the urine excreted from the body of a test subject administered with ALAs, detection of urothelial cancer is possible. Further, they also found out that the dosage amount of ALAs was sufficient in an extremely small amount such as less than a half of the amount used for conventional determination of the excision site. The present invention has been thus completed.

Specifically, the present invention relates to (1) a method for detecting urothelial cancer comprising administering 5-aminolevulinic acid (ALA), a derivative thereof, or a salt of these to a test subject, collecting urine from the test subject, and detecting fluorescence in a cell of the collected urine; (2) a method for detecting urothelial cancer comprising separating a cell from urine collected from a test subject administered with 5-aminolevulinic acid (ALA), a derivative thereof, or a salt of these, and detecting fluorescence in the separated cell; (3) the method for detecting urothelial cancer according to (1) or (2), comprising administering 5-aminolevulinic acid (ALA), a derivative thereof, or a salt of these in an amount of 0.05 to 20 mg per kg of a test subject in ALA hydrochloride equivalent; (4) the method for detecting urothelial cancer according to (1) or (2), comprising orally administering 5-aminolevulinic acid (ALA), a derivative thereof, or a salt of these; (5) the method for detecting urothelial cancer according to (1) or (2), wherein the test subject is a human suspected to have urothelial cancer; and (6) an agent for detecting urothelial cancer, comprising 5-aminolevulinic acid (ALA), a derivative thereof, or a salt of these to be used in the method according to (1) or (2).

Effect of the Invention

According to the present invention, no particular culture apparatus is needed, and a determination just after urine collection is possible. Further, as it can be determined that there is an abnormality when fluorescence in cells in the urine is detected, it can be immediately transferred to diagnosis through an endoscope or to transurethral resection. For example, by performing the fluorescence detection test in the cells in the urine before an endoscopic examination for determining the presence or absence of relapse, if there is no suspicion, there is no need to go through an endoscopic examination. This significantly reduces burden of patients, which will also lead to reduction of national medical expenses. As such, the method of the present invention allows rapid and simple detection with high accuracy of not only bladder cancer but all urothelial cancers, which is a remarkable technique in the medical services of this field. Further, as the detection is possible with a small dosage amount of ALAs, it is advantageous economically, and there is also an effect in security that photolesion is substantially not caused.

BRIEF DESCRIPTION OF DRAWINGS

FIG. 1 It is a fluorescence microscopy photograph of cells separated from the urine when 1 g ALA hydrochloride is administered.

FIG. 2 It is a fluorescence microscopy photograph of cells separated from the urine when 500 mg ALA hydrochloride is administered.

MODE OF CARRYING OUT THE INVENTION

The method for detecting urothelial cancer of the present invention is not particularly limited as long as it is a method comprising administering 5-aminolevulinic acid, a derivative thereof, or a salt of these (ALAs) to a test subject, collecting urine from the test subject, and detecting fluorescence in the cells in the collected urine (for example detection of the presence of fluorescence or amount of fluorescence); or a method comprising separating a cell from a urine collected from a test subject administered with 5-aminolevulinic acid, a derivative thereof, or a salt of these (ALAs), and detecting fluorescence in the separated cell. The method for detecting urothelial cancer of the present invention encompasses a method for collecting data for detection. Further, the agent for detecting urothelial cancer of the present invention is not particularly limited as long as it comprises ALAs used in the above-mentioned method of the present invention. Further, the urothelial cancer which is the target of detection in the present invention is a malignant tumor developed from transitional epithelia covering the inner cavity of urinary tract (kidney, renal pelvis, urinary duct, bladder, and urethra). Furthermore, the test subject of the present invention relates to mammals including human, and specifically human being suspected of having urothelial cancer from a medical examination such as medical interview can be exemplified.

Among ALAs, an ALA derivative is exemplified by those ALAs having an ester group and an acyl group, where the preferred examples include the combinations of methyl ester group and formyl group, methyl ester group and acetyl group, methyl ester group and n-propanoyl group, methyl ester group and n-butanoyl group, ethyl ester group and formyl group, ethyl ester group and acetyl group, ethyl ester group and n-propanoyl group, and ethyl ester group and n-butanoyl group.

Among ALAs, examples of a salt of ALA or its derivative include: an acid addition salt such as hydrochloride, hydrobromate, hydroiodide, phosphate, nitrate, hydrosulfate, acetate, propionate, toluenesulfonate, succinate, oxalate, lactate, tartrate, glycolate, methanesulfonate, butyrate, valerate, citrate, fumarate, maleate and malate; a metallic salt such as sodium salt, potassium salt and calcium salt; ammonium salt; and alkylammonium salt. When for use, these salts are used in the form of a solution and act in a similar manner to ALA and its derivatives.

Among these ALAs, 5-aminolevulinic acid; and 5-aminolevulinic acid methyl ester, 5-aminolevulinic acid ethyl ester, 5-aminolevulinic acid propyl ester, 5-aminolevulinic acid butyl ester and 5-aminolevulinic acid pentyl ester, or their hydrochloride, phosphate, hydrosulfate, etc. are preferred. ALAs mentioned above may form a hydrate or a solvate and may be used either alone or in appropriate combination of two or more kinds.

The ALAs can be produced by any known method such as production by chemical synthesis, production by microorganisms, and production using enzymes. When producing by microorganisms or using enzymes, it can be used as it is without purification, unless it contains any inconvenient inhibitor.

The dosage amount of these ALAs to a test subject is for example 0.02 to 50 mg per 1 kg of a test subject in ALA hydrochloride equivalent, preferably 0.05 to 20 mg, more preferably 0.2 to 10 mg, and furthermore preferably 5 to 10 mg.

As methods for administering ALAs in the method for detecting urothelial cancer of the present invention, oral administration including sublingual administration, intravenous administration including drip infusion, transdermal administration using a poultice and the like, suppository, drip infusion, etc. can be exemplified. From the viewpoints of reducing patients' burden or improving sensitivity of fluorescence, oral administration is preferred.

The agent for detecting urothelial cancer of the present invention comprising the ALAs can contain, as necessary, other ingredients such as other medicinal ingredients, nutrients, carriers, etc. As a carrier that can be blended with the detecting agent of the present invention, an organic or inorganic, solid or liquid, pharmacologically acceptable carrier material, which is suitable for intake and is generally inactive, can be used. Specific examples of such a carrier include crystalline cellulose, gelatin, lactose, starch, magnesium stearate, talc, vegetable or animal fat, fat and oil, gum and polyalkylene glycol. Examples of dosage forms of orally administered agents include powders, granules, tablet, capsule, syrup and suspension. These preparations can be produced using a solvent, a disperser, a thickener, an excipient, etc., as appropriate, according to an ordinary method. When preparing the detecting agent of the present invention as an aqueous solution, it is preferred to prepare so that it does not become alkaline in order to prevent decomposition of ALAs. If it is alkaline, decomposition can be prevented by removing oxygen.

The method for detecting urothelial cancer of the present invention allows to detect urothelial cancer by collecting urine after administering ALAs (the detecting agent of the present invention), and detecting the presence or absence of fluorescence or the amount of fluorescence in the cells in the collected urine with a fluorescence microscope, etc. Further, by further adding ALAs to the collected urine, leaving it for a predetermined time according to need, and detecting the presence or absence of fluorescence or the amount of fluorescence, the sensitivity can be further improved. According to the method for detecting urothelial cancer of the present invention, detection (determination) of urothelial cancer can be mechanically performed based on the presence of fluorescence, one without any particular knowledge such as a medical doctor, can easily make the detection. Further, detection can be made using an apparatus.

For the collection of urine, it is preferred that the urine is the first discharged after administering ALAs (the detecting agent of the present invention). It is more preferred to collect urine after 1 hour and within 12 hours after the administration, and more preferably after 2 hours and within 12 hours. The method of taking urine is not limited, and can be from spontaneous urination or collection by catheter.

When detecting fluorescence in the cells, cells are separated from urine by centrifugation or filtration, similarly as for normal cytology. When detecting fluorescence, excitation light containing ultraviolet rays comparable to Soret band to visible rays of violet to blue is irradiated, and generated fluorescence is detected with fluorescence microscope, etc.

EXAMPLES

The present invention will be more specifically described in the following examples. However, these examples are not intended to limit the technical scope of the present invention.

Example 1

1 g of ALA hydrochloride was dissolved in 50 ml of orange juice, and was given to a patient suspected of having bladder cancer (body weight about 60 kg). Urine was collected after about 4 hours, which was immediately centrifuged (3000 rpm/min., 15 min.) in a light shielded state, and was confirmed by microscopic visualization using sediments. The results are shown in FIG. 1. The microscope used was OLYMPUS BX50CCD mounted with camera OLYMPUS DP70. The mirror set was Exciter: XF1076 400AF30 Dichroic:XF2007 475DCLP, Emitter: XF3090 585ALP (OMEGA OPTICAL), all of which being a standard fluorescence microscope system.

As it is clear from FIG. 1, a clear PPIX fluorescence derived from cancer cell was observed. From a normal pathological diagnosis of the cells, it was shown to be cancer cells.

From the above, it has been revealed that according to the method of the present invention, urothelial cancer can be detected by detecting fluorescence of the cells in the urine, without observing in the bladder as in the conventional way. When orally administering ALAs, as ALAs are supplied to cancer affected areas from blood, conventionally, it was not assumed that PPIX derived from ALAs accumulates not only in cancer affected areas but also in cancer cells exfoliated from cancer affected areas. However, actually, PPIX derived from ALAs were accumulated in cancer cells in the urine exfoliated from cancer affected areas, and an unexpected result was obtained that by detecting fluorescence in the cells in the urine, urothelial cancer can be detected.

Example 2

The detection method was performed in the same way as Example 1, except that the dosage amount was changed to 500 mg, which is the half amount of Example 1. As a result, the picture of FIG. 2 was obtained. From a normal pathological diagnosis of the cells, it was shown to be cancer cells.

INDUSTRIAL APPLICABILITY

The method for detecting urothelial cancer of the present invention allows a very rapid, simple and accurate detection with fewer burdens to a patient, and as the dosage amount of ALAs suffices with half of the conventional amount, there is an economic merit. Further, as the risk of vomiting, liver impairment, and photosensitivity which are sometimes observed can be substantially eliminated, it can be said to be a remarkable method that contributes to an early detection of urothelial cancer.

The invention claimed is:

1. A method for detecting urothelial cancer comprising orally administering 5-aminolevulinic acid (ALA), a derivative thereof, or a salt thereof to a test subject, collecting a urine sample by a natural urination from the test subject after the oral administration of 5-aminolevulinic acid (ALA), the derivative, or the salt, separating a cell from the urine sample, and detecting fluorescence in the separated cell.

2. The method for detecting urothelial cancer according to claim 1, comprising orally administering 5-aminolevulinic acid (ALA), the derivative, or the salt to the test subject in an amount of 0.05 to 20 mg per kg of the test subject in ALA hydrochloride equivalent.

3. The method for detecting urothelial cancer according to claim 1, wherein the test subject is a human suspected to have the urothelial cancer.

4. The method for detecting urothelial cancer according to claim 2, wherein the subject is a human.

5. The method according to claim 1, wherein the collected urine is the first urine discharge after the oral administration of 5-aminolevulinic acid (ALA), the derivative, or the salt.

6. The method according to claim 1, wherein the step of assaying for fluorescence is performed by microscopic visualization.

7. The method according to claim 1, wherein the collection of urine is performed after 1 hour and within 12 hours after the administration of 5-aminolevulinic acid (ALA), the derivative, or the salt.

8. A method of detecting urothelial cancer comprising:
orally administering 5-aminolevulinic acid (ALA), a derivative thereof, or a salt thereof to a subject,
collecting urine by a natural urination from the subject,
separating a cell from said urine, and
assaying said cell for fluorescence,
wherein said assaying occurs immediately after said cell separation.

9. A method of detecting urothelial cancer comprising orally administering 5-aminolevulinic acid (ALA), a derivative thereof, or a salt of ALA or the derivative to a subject,
collecting a urine sample by a natural urination from the subject after the oral administration of 5-aminolevulinic acid (ALA), the derivative, or the salt,
irradiating a cell in the urine sample, and
detecting fluorescence from a metabolite of ALA in said cell,
wherein positive detection of fluorescence indicates the presence of urothelial cancer in the subject.

* * * * *